United States Patent [19]

Slivenko

[11] 4,092,983

[45] June 6, 1978

[54] BLOOD ACCESS DEVICE

[75] Inventor: Victor Slivenko, San Diego, Calif.

[73] Assignee: General Atomic Company, San Diego, Calif.

[21] Appl. No.: 764,207

[22] Filed: Jan. 31, 1977

[51] Int. Cl.² ............................................. A61M 5/00
[52] U.S. Cl. .................................. 128/214 R; 128/348
[58] Field of Search ............... 128/214 R, 214 B, 274, 128/334 R, 348, 350 R, 1 R

[56] References Cited

U.S. PATENT DOCUMENTS

| 2,935,068 | 5/1960 | Donaldson | 128/348 |
| 3,505,991 | 4/1970 | Hellerstein et al. | 128/1.1 |
| 3,663,965 | 5/1972 | Lee et al. | 128/348 X |
| 3,765,032 | 10/1973 | Palma | 128/348 X |
| 3,783,868 | 1/1974 | Bokros | 128/348 X |
| 3,815,577 | 6/1974 | Bucalo | 128/1 R |
| 3,998,222 | 12/1976 | Shihata | 128/214 R |
| 4,015,601 | 4/1977 | Bokros et al. | 128/214 R |

Primary Examiner—Dalton L. Truluck
Attorney, Agent, or Firm—Fitch, Even, Tabin & Luedeka

[57] ABSTRACT

A device to provide access to the circulatory system of a living body for simultaneous withdrawal and return of blood to the system includes a pair of parallel tubular conduits and a housing integrally associated with the conduits and having fluid communication therewith through apertures in the conduit walls located at points where the conduits adjoin the housing. The housing extends the fluid communication to a point outside the living body. Inside the housing is a movable valve body which has a pair of ports alignable with the respective apertures. The valve body is movable in the housing between positions of alignment and nonalignment of the apertures and respective ports to selectively establish fluid communication between the circulatory system and the outside of the living body. At least the surfaces of all parts of the device that contact blood and tissue are made of biologically compatible material.

16 Claims, 12 Drawing Figures

BLOOD ACCESS DEVICE

This invention relates to medical devices and, more particularly, to a device to provide access to the circulatory system of a living body for simultaneous withdrawal and return of blood to the circulatory system.

There is a need for a device to provide accesss to the circulatory system of a living body in circumstances requiring, for example, simultaneous withdrawal and return of blood from the circulatory system while passing the blood externally through a blood dialyzer. An individual could require this over an extended period of time, and it is desirable for a device in the form of an implant to be available in the body for immediate connection of catheters to the circulatory system at any desired time. As an implant, however, such a device should be biologically compatible with the living tissues surrounding it. In this connection, the device should not prevent healing, irritate tissues, or stimulate a prolonged rejection response by the living body. Further, the device should be physiologically inert over prolonged periods of time and should be mechanically strong and reliable.

In copending application Ser. No. 622,090, filed Oct. 4, 1975, now U.S. Pat. No. 4,015,601 issued Apr. 5, 1977, and assigned to the assignee of this invention, an access device is described which provides means for forming fluid communication between the outside and the circulatory system, but for fluid passage in one direction at a time. It is desirable also to have a device that will provide access to the circulatory system for simultaneous withdrawal and return of blood to the system.

Accordingly, it is a primary object of this invention to provide a device for insertion into a blood vessel of the circulatory system that will afford access to the blood stream or simultaneous withdrawal and return of the blood.

It is a further object of this invention to provide such a device that is biologically compatible with the living tissues surrounding the device without irritating the tissues.

It is another object of this invention to provide a device of the aforementioned type that is physiologically inert over long periods of time and is mechanically strong and reliable.

The accomplishment of these and other objects of the invention will become apparent from the following description and its accompanying drawings of which.

The device of the invention includes three principal outer portions, two of which are generally parallel to one another and the other of which is generally at right angles to the two parallel portions. Both parallel portions are tubes having open ends. Either one may be inserted longitudinally in a blood vessel, the other being available for connection to a bypass in the form of a graft either upstream or downstream of the same blood vessel. The third major portion is a housing with one end open and the other closed, the housing containing a valve for establishing fluid communication with the blood in the blood vessel. The valve is adapted to receive a dual-conductor catheter which is used to establish a blood flow line simultaneously in and out of the circulatory system. The device is structured of materials that are biologically compatible with the blood and tissues of a living body in which it is inserted. At least all blood contacting surfaces are carbon. Further, the material is physiologically inert over prolonged periods of time and is mechanically strong and reliable, all of which is described in detail hereinafter.

Figure 1:
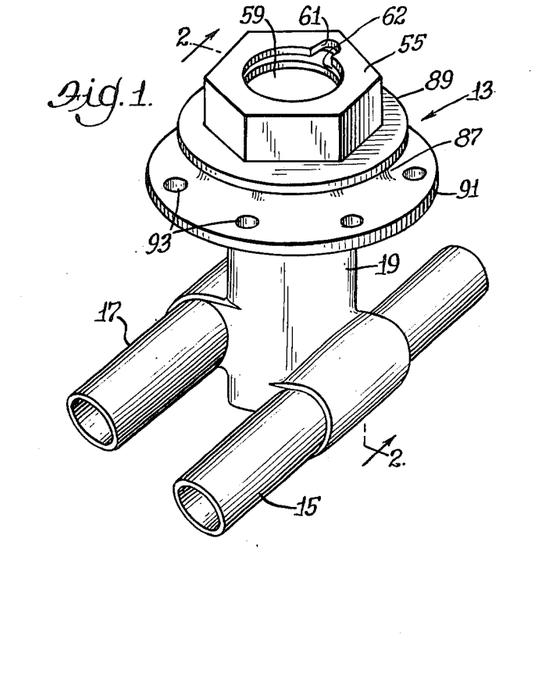
FIG. 1 is a perspective view of a blood access device embodying various features of the invention and adapted for implantation in a living body.

Referring now to FIG. 1, there is shown a blood access device 13 having a pair of parallel conduits 15 and 17 and a housing 19 having a closed end 20, the conduits being adjoined near the closed end. In this illustrated embodiment, both the conduits 15 and 17 are round tubular open-ended structures, and the housing 10 is generally cylindrical in form. The conduits 15 and 17 are generally parallel to one another and are generally at right angles to the axis of the housing 19.

Figure 2:
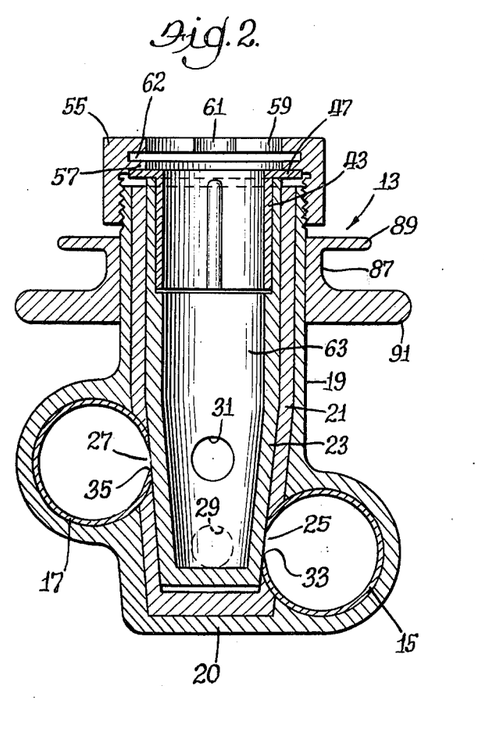
FIG. 2 is a vertical sectional view of the device of FIG. 1 taken along the line 2—2 and illustrating parts nonaligned (valve closed) to prevent fluid communication.

In FIG. 2 it will be seen that several members are mounted internally of the housing 19. Immediately inside the walls of the housing 19 is a liner 21, and immediately inside the liner 21 is a valve body 23. It will be noted that the housing 19 is generally cylindrical with the inner portion of the housing being tapered toward its closed end. Both the liner 21 and valve body 23 are generally cylindrical, each having a closed end and an open end. They both taper inwardly toward their closed ends, the respective tapers conforming to that of the housing interior. The liner 21 forms a snug or close-fitting relation with the internal portion of the housing 19, as does the valve body 23 within the liner 21. Nonetheless, the valve body is coaxially rotatable within the liner 21 and housing 19, the liner being fixed to the housing interior by a suitable epoxy or cement. The liner 21 is dimensioned so that it will completely line the interior wall of the housing 19 and fit against the closed end of the housing. It is important that the valve body 23 form a tight seal with the liner 21, and for this reason, the closed end of the valve body 23 does not bottom on the interior end of the liner 21. Clearance is provided to assure adequate seating of the valve body within the liner along the tapered interface to form, as will be described in detail hereinafter, a liquid and bacterial seal. Some very slight differences in diameters of the respective parts can be tolerated with this tapered structure. Preferably, both the valve body 23 and the liner 21 are made of pyrolytic carbon and the housing 19 is made of titanium, as fully described hereinafter.

Figure 3:
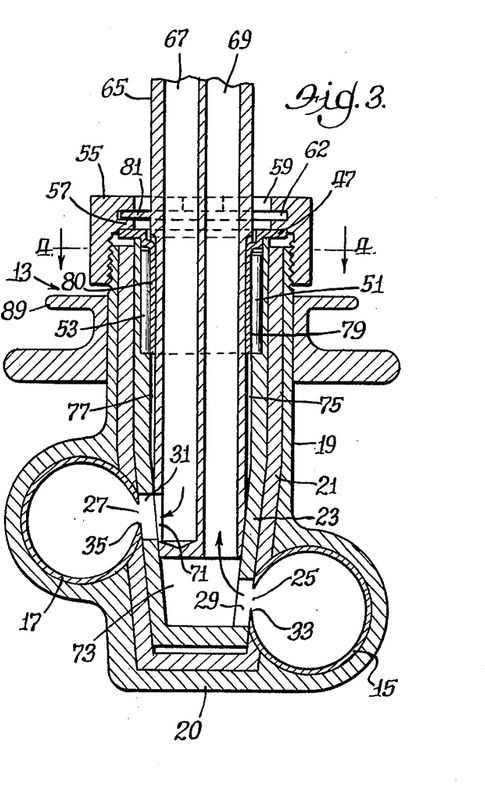
FIG. 3 is a view similar to FIG. 2, but illustrating parts aligned (valve open) for fluid communication and illustrating one form of a catheter inserted in the device to extend the communication externally of the body.
Figures 5, 5A, 6, 7, 8, 9, 10, 11:
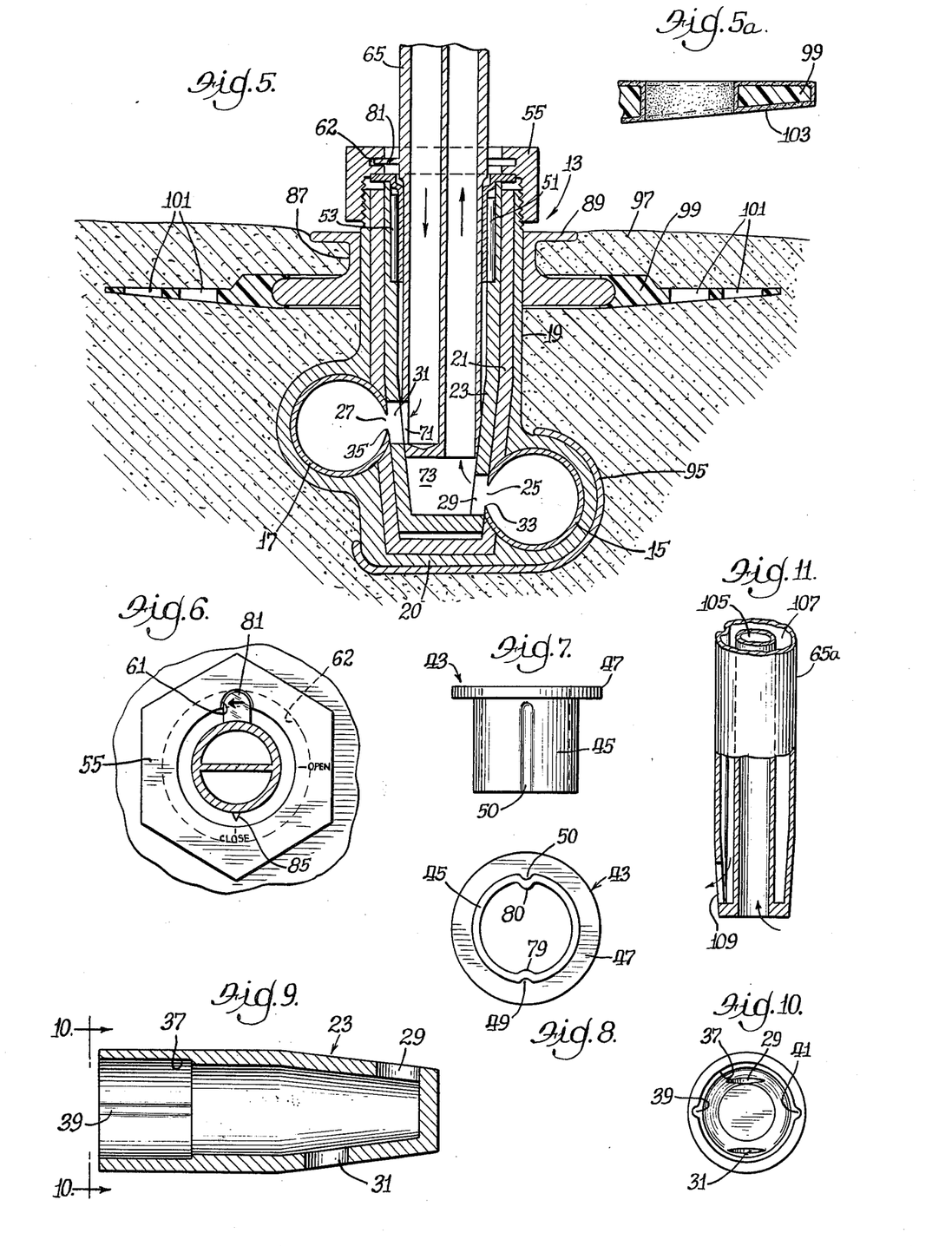
FIG. 5 is a view similar to FIG. 3 and showing the device in the environment of a living body and including a ring flange to enhance the implantation of the device.
FIG. 5a is an enlarged view of a portion of the ring flange illustrating a coating on all surfaces.
FIG. 6 is an end view of the device with part in section.
FIG. 7 is a side view of a catheter receiving member of the device.
FIG. 8 is an end view of the member of FIG. 7.
FIG. 9 is a sectional view of a valve member of the device.
FIG. 10 is an end view of the device taken along the line 10—10 of FIG. 9.
FIG. 11 is an alternative construction of a catheter tip suitable for insertion in the device.

FIG. 2 shows the device 13 with the valve body 23 in the closed position, i.e., there is no fluid communication between the interiors of both the conduits 15 and 17 and the interior of the valve body 23. To provide such fluid communication between these interiors, the conduits 15 and 17 are provided with apertures 25 and 27 respectively through the conduit walls. Although the conduits 15 and 17 are generally parallel to each other, their points of adjoining the housing are displaced from each other with respect to the axis of the housing 19, as well as being spaced away from the axis itself. Accordingly, the apertures 25 and 27 are spaced apart from each other axially of the housing 19, and to complete the fluid communication to the interior of the valve body 23, there are provided ports 29 and 31 in the wall of the valve body located to be alignable with the apertures 25 and 27 at a given rotative position of the valve body 23. Referring briefly to FIGS. 3 and 5, such alignment is seen. Because of the axial displacement of these apertures and their corresponding ports, there is only one rotative position of the valve body in which fluid communication will be established between the interiors. Referring once again to FIG. 2, the valve body is shown with a 90° rotation from the position of alignment, but even at a 180° rotation from the position of alignment, it will be seen that fluid communication will not be established. The apertures 25 and 27 are each defined by a perimeter formed of a sharp edge 33 and 35 respectively of the conduit walls.

The valve body 23 with its ports 29 and 31 is shown separately in FIG. 9. There it will be seen that a counterbore 37 is provided in the open end of the body. FIG. 10 is a view looking into the open end of the valve body 23, and it will be seen that a pair of grooves 39 and 41 are provided in the inner surface of the counterbore 37. These grooves are coterminous with the counterbore and extend in a direction axially of the valve body.

The purpose of the counterbore 37 is to receive and hold a cannula receptacle shown in FIGS. 7 and 8. This receptacle includes a cylindrical body 45 and a top flange 47. The body 45 has an outside diameter that forms a snug fit when the receptacle is inserted in the counterbore 37 at the open end of the valve body 23.

A suitable epoxy or other cement is used to affix the cannnula receptable 43 to the valve body 23 after the desired rotative position of the receptacle with respect to the valve body has been established. This desired position involves a pair of grooves 49 and 50 in the outer surface of the body wall 45 extending in a direction axially of the cannula receptacle. The grooves 49 and 50 are in the outer surface of the body wall and are semicircular in cross section. The grooves 39 and 41 are in the inner surface of the counterbore 37 are semicircular in cross section and are substantially of the same diameter as the grooves 49 and 50. When the receptacle 43 is inserted in the counterbore 37, the receptacle is rotated until the grooves in the receptable oppose the grooves in the counterbore, thus forming two cylindrical openings at these locations extending in a direction axially of the combined cannula receptacle 43 and valve body 23.

Figure 4:
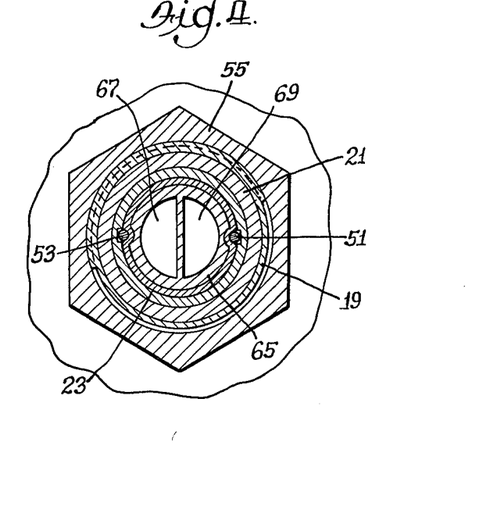
FIG. 4 is a cross-sectional view of the device taken along the line 4—4 of FIG. 3.

Referring now to FIGS. 3 and 4, a pair of rods 51 and 53, preferably of stainless steel, are inserted in the cylindrical openings formed by the opposing grooves, the suitable epoxy first having been applied to the interface between the cannula body wall 45 and the valve body counterbore 37. The relationship between the receptacle 43 and the valve body 23 then becomes fixed. As will be seen hereinafter, the cannula receptacle 43 is instrumental in causing the rotation of the valve body 23 between positions of alignment and nonalignment of the apertures and ports to selectively establish fluid communication therethrough, and the stainless steel rods form an interlock in the opposing grooves as a safety feature in the event the epoxy should for any reason let loose. The rods thus assure unison rotative movement between the cannula receptacle and the valve body whenever rotative force is applied to the cannula receptacle, which occurs with the aid of a catheter as described hereinafter.

A cap 55 is applied over the open end of the housing 19, the liner 21, and the valve body 23, including the affixed cannula receptacle 43. The cap 55 is of a screw type, and the outer surface of the housing 19 near its open end is threaded to accommodate the cap 55. A shoulder 57 on the interior of the cap 55 bears down upon the flange 47 of the cannula receptacle to securely retain the valve body 23 affixed to the receptacle in a seated position within the liner and housing.

As best seen in FIG. 1, the cap 55 is provided with a generally circular orifice 59 having a key slot 61 extending outwardly from a point along its general circumference. The key slot serves as an entrance to a circumferential slot 62 formed in the inner wall of the cap 55, the purpose of which is described hereinafter. A generally longitudinal pasage 63 (FIG. 2) begins at the orifice 59 and extends through the cannula receptacle 43 to the closed end of the valve body 23.

Referring now to FIG. 3, this longitudinal passage 63 receives a catheter 65 inserted to establish a flow path for the blood when blood passage is established by alignment of the ports 29 and 31 with the apertures 25 and 27 respectively in accordance with the invention. The catheter 65 is tapered on its end outer surface to conform to the interior tape of the longitudinal passage 63 in the interior closed end portion of the valve body 23. To effect simultaneous withdrawal and return of blood from the living body, the catheter 65 is of dual-conduit design, having a pair of side-by-side conduits 67 and 69. The conduit 67 is closed at the tip of the catheter, and fluid communication to the port 31 of the valve body 23 is established through a side port 71 of the catheter wall positioned to align with the port 31 when the catherter tip is completely inserted. The conduit 69, on the other hand, is open-ended and provides immediate fluid communication with a cavity 73 at the closed end of the valve body 23 between the top of the catheter and the inside end of the valve body. The port 29 is, of course, in communication with the cavity 73, and a fluid flow is thus established from the interior of the conduit 15 to the conduit 69 when the port 29 is aligned with the aperture 25 in the wall of the conduit 15.

Although arrows in FIG. 3 indicate a directional flow from the interior of the conduit 15 outwardly through the conduit 69 and return through the conduit 67 to the interior of the conduit 17, it should be understood that this is for the purpose of depicting a simultaneous outward and return flow of a fluid in the blood access device 13, rather than for stressing a particular direction of flow. The direction of both arrows could be reversed to indicate a reverse direction of flow in accordance with the invention.

The catheter 65 is inserted into the longitudinal passage 63 when the valve is closed, i.e., when the ports 29 and 31 are in a nonaligned relation with the apertures 25 and 27 respectively. To establish a passage for blood in accordance with the invention, the catheter 65 is used as an instrument to rotate the valve body 23 to align the port with the apertures. After such rotation, the valve is open and a passage for blood is established.

To effect such rotation of the valve body by the catheter 65, the catheter tip is further provided with a pair of flutes 75 and 77 in the outer walls of the catheter tip that are located 180° from each other, and a pair of longitudinal guides 79 and 80 (FIG. 8) are located on the back sides respectively of grooves 49 and 50 in the body wall 45 of the cannula receptacle 43. Accordingly, before the catheter 65 can be inserted in the longitudinal passage 63, the catheter must be rotated to align the flutes 75 and 77 with and thus engage the longitudinal guides 79 and 80 upon insertion of the catheter. Because the cannula receptacle which the catheter thus engages is affixed to the valve body 23, the valve body will be rotated upon rotation of the catheter.

It would be completely undesirable for the catheter 65 to be removable when the valve is open and blood is flowing. The avoid such a circumstance, a lug 81 extending at right angles outwardly from the catheter wall is provided on the catheter 65. As best seen in FIG. 6, this lug is shaped and sized to pass freely through the key slot 61 in the cap 55, when the valve is closed and the catheter is aligned for insertion therein. The circumferential slot 62 provided in the cap 55 receives the lug 81 and retains the catheter 65 in its seated position when the catheter is rotated to open the valve. Thus, it may be seen in FIG. 1 that the insertion of the catheter 65 will stop after the lug 81 has entered and passed through the key slot 61. Rotative movement to open the valve thereafter occurs.

Referring once again to FIG. 6, the cap 55 is also provided with indicia to indicate the particular relative rotative positions of the catheter 65 and the cap 55. A small protrusion 85 in the form of a pointer is provided on the catheter at a position 180° from the lug 81 and a mark with the word "open" or the like is provided on the top surface of the cap at a point to which the catheter 65 must be rotated to effect the opening of the valve. Because the lug 81 at that point is secure in the slot 83, the catheter can only be removed when the valve is closed by a rotation of the catheter adequate to align the lug 81 with the key slot 61 for removal. Thus, to interrupt the blood passage, the catheter 65 is rotated at least one-quarter of a turn, and at this point the ports and the apertures are not aligned. Because of the close-fitting, seated relation of the valve body 23 with the liner 21, there is a liquid and bacterial seal established around the sharp edges 33 and 35 respectively of the apertures 25 annd 27, as is more completely described hereinafter. The bacterial seal is a barrier to the invention of bacteria in the blood stream through the interfaces of the moving parts of the blood access device 13.

Returning to FIG. 1, around the perimeter of the housing 19 is a stabilizing button 87 that has the appearance in a sectional view (e.g., FIGS. 2, 3 and 5) of a collar button, a smaller flange 89 being at one end of the button and a larger flange 91 being at the other end. In practice, this button is applied over the housing such that the smaller flange 89 will be disposed at the approximate level of the skin surface. These flanges on the button project outwardly from the housing, and the larger flange 91 carries a plurality of holes 93. When the blood access device 13 in implanted in a human body, body tissue will grow in and around the holes 93 and stabilize the position of the blood access device in the body. The position of the button 87 may be movable axially of the housing to control the extent the housing extends beyond the surface of the skin, or the position of the button may be fixed if uniformity of housing height above the flange is found to be desirable. Further, it may be desirable to also include an epithelium stopping means in the form of another collar (not shown) between the flanges 89 and 91, as described in U.S. Pat. No. 3,783,868, issued Jan. 8, 1974, to inhibit the progressive growth of epithelium tissue down and around the housing 19.

In FIG. 5, the device 13 is illustrated as implanted in a living body, and the conduit 15 is shown in an inserted relation with a blood vessel, such as an artery 95. It should be recognized that although the blood access device 13 is useful in a living human body, it may also have veterinary or scientific applications in other living animals, domestic or wild. Further, although its use is shown in an artery, it should be understood that this is for illustration only and that the device of the invention may be inserted in any part of a circulatory system as needed, and there is no intention of limiting its use to an artery.

The device 13 is inserted in the living body by any suitable surgical procedure. Generally, a longitudinal incision is made through the skin at the desired location for insertion in the blood vessel, and in incision is made in the blood vessel after momentarily stopping the flow of blood therethrough. Sutures (not shown) are then used to sew up the blood vessel after the ends of the conduit 15 have been inserted therein, and other sutures (not shown) are used to sew up the skin around the housing 19 as illustrated. In this connection, it is noted that the length of the housing 19 above the point of association with the conduit 15 is sufficient to extend from the blood vessel in which the conduit 15 is inserted to a point outside the living body, i.e., outside the skin layer 97. Alternatively, the artery 95 may be severed and the severed ends slipped over the protruding ends of the conduit 15 without engaging the device housing 19. The conduit 17 is then connected to the circulatory system by a graft at points upstream or downstream from the incision and insertion of the conduit 15. Although for purposes of description, the conduit 15 has been described and illustrated as being inserted in the blood vessel, and the conduit 17 as being connected to the graft, it is in accordance with the invention that the conduit 17 could be inserted in the blood vessel and conduit 15 connected to the graft, at the option of the surgeon.

To enhance particularly a rotative stabilized position of the device 13 in the human body, a flexible flange 99 is provided that attaches over the circumference of the larger flange 91 of the button 87. It, also, has a plurality of holes 101 through its surface. Body tissue will grow in and around these holes 101 and stabilize particularly the rotative position of the blood access device 13. The flange 99, as discussed hereinafter, is more flexible than the flange 91 on which it is mounted, and thus affords a larger diameter for securing the rotative position without the larger diameter being rigid and possible adversely affecting the insertion in the blood vessel.

As shown in FIG. 5a, all surfaces of the flexible flange 99 are covered with a thin coating 103 of carbon as described in detail hereinafter.

An alternative construction of a dual-conduit catheter is illustrated in FIG. 11 by catheter 65a. Here the two conduits are arranged concentrically rather than side-by-side while the external construction is fluted and tapered the same as the catheter 65 described previously. Thus, a conduit 105 is open-ended and forms the center conduit, and a conduit 107 is concentric with the conduit 105, but is closed-ended and has its opening a port 109 in its side wall. Referring briefly again to FIG. 3, it will be seen that this alternative catheter 65a may be inserted in the same manner as the catheter 65, it being understood that the alternative catheter 65a will have a pair of flutes and a lug the same as the flutes 75 and 77 and lug 81 of the catheter 65. It should be understood also that when the alternative catheter 65a is inserted in the blood access device 13, the port 109 will align with the port 31 in the valve body 23, and so the conduit 107 will have fluid communication with the interior of the conduit 17, whereas the conduit 105 will have fluid communication through the cavity 73 to the interior of the conduit 15.

As mentioned previously, because the blood access device 13 is inserted within a living body, it is important that the material of the device be biocompatible (biologically compatible) with the blood and living tissues which surround it. Furthermore, the device, once inserted, should not prevent healing, irritate tissues, or stimulate a strong or prolonged rejection response by the living body, and the material of the device should be physiologically inert over long periods of time in addition to being mechanically strong and reliable.

In accordance with the invention, a coating of carbon is utilized on all blood contacting surfaces and on the housing/skin interface. This carbon coating may be pyrolytic carbon, vapor-deposited carbon or vitreous carbon, and these kinds of coatings may be utilized on different parts of the blood access device 13. Pyrolytic carbon, vitreous (glassy) carbon, and vapor-deposited carbon are compatible with the surrounding tissues over prolonged time periods when inserted through the skin layer of a living body. Preferably, pyrolytic carbon and/or vapor-deposited carbon are used. These coatings do not tend to irritate the surrounding skin tissues and they promote the establishment of a barrier to external pathogens.

In general, the preferred construction of the device 13 includes a metallic housing, such as titanium, stainless steel or a chromium-cobalt alloy such as VITALLIUM. Preferably, the housing is constructed of titanium. The conduits 15 and 17 are constructed of pyrolytic carbon and may be formed in any suitable manner, such as deposition of a built-up coating on a mandrel, after which the mandrel is removed, leaving the tube-like structures. Both the liner 21 and the valve body 23 are constructed by preshaping a suitable substrate, such as a graphite core, in the general form of a cylinder and having one end taper gradually to a reduced diameter. A coating of the pyrolytic carbon is then made thereon, and the graphite is removed, as by drilling, leaving a pyrolytic carbon shell. The interfacial surfaces, particularly of the tapered portions, are lapped and polished to enhance a close-fit relation with adjacent parts. The ports are then made in a suitable manner, as by drilling. The button 87 also is constructed on a suitable substrate or graphite core which is preshaped to the desired form, which includes both the smaller flange 89 and the larger flange 91, the holes 93 then being formed in the flange 91, such as by drilling, and a pyrolytic carbon coating being applied to the core, including the inner surfaces of the holes 93. Preferably, on this button the carbon coating has a rough finish. The core materials and the process of applying the pyrolytic carbon coatings are described in detail hereinafter.

The cannula receptacle 43 preferably is made from stainless steel and formed in a suitable manner, such as by a stamping and drawing operation. The cap 55 is machined in a suitable manner, preferably from stainless steel, as are also the interlocking rods 51 and 53 (FIG. 4). The flexible flange 99 (FIG. 5) preferably is of molded polypropylene with a suitably applied carbon coating 103 on all surfaces, including the inner surfaces of the holes 101.

One such blood access device 13 has been constructed in which the overall length of the housing 19 is approximately 0.8 inch and its outer diameter is approximately 0.35 inch. The location of the conduit 17 with respect to the open end of the housing 19 is such that the axis of the conduit 17 is approximately 0.5 inch from the open end. The overall diameter of the larger flange 91 is approximately 0.75 inch and the overall diameter of the flexible flange 99 (FIG. 5) is approximately 1.5 inches. The holes 93 in the flange 91 and the holes 101 in the flange 99 are 0.1 inch in diameter. The pyrolytic carbon wall thickness of both the liner 21 and the valve body 23 is approximately 0.03 inch. The diameter of the longitudinal passage 63 inside the valve body 23 is 0.19 inch, and from such diameter the walls taper inwardly at an angle of 5° 45′. The interlocking stainless steel rods 51 and 53 are 0.01 inch in diameter and are approximately 0.2 inch long.

These dimensions are provided by way of giving an example of construction, but there is no intention of requiring the construction to be limited to any of these dimensions.

As seen in FIGS. 2, 3 and 5, when the conduits 15 and 17 are inserted and joined to the housing 19, the side walls of the conduits intersect the liner 21 and valve body 23. The portion of the conduit wall that would intersect the valve body 23 is formed in a suitable manner, as by grinding, to conform to the general shape of the circular outer surface of the valve body 23 to form a seat for the valve. The interfacial surfaces are then lapped and polished to form a good seal therebetween in this snug or close-fitting relation. In this connection, a very important step in making the blood access device 13 is the lapping of the portion of the external surface of the conduits 15 and 17 that are in contact with the valve body 23 to conform these portions to the circular surface of the valve body so as to produce the sharp edges 33 and 35 (FIGS. 2 and 3) as well as seats for the valve. Such a sharp edges does not permit the accumulation and coagulation of blood around the aperture. Thus, after having once established fluid communication between the artery 41 and the catheter 65 or 65A and then closing the valve body by rotation thereof, the blood flow will be cleanly interrupted with no places for accumulation or coagulation of the blood in the conduits 15 and 17. After the valve is closed, any residual blood in the valve body 23 may be flushed out by using a suitable cleansing solution. Thereafter, a suitable plug (not shown) may be applied over the end of the cap 55 to keep the interior clean until next use.

The pyrolytic carbon may be deposited upon the mandrels in the instance of the conduits 15 and 17 and upon the core materials for the other parts in the manner described in U.S. Pat. No. 3,783,868 and U.S. Pat. No. 3,298,921. An example of a coating method that may be employed is that of supporting the formed substrate on a rotating or stationary mandrel within a large fluidized bed, is discussed in the aforementioned patents, or coating on freely moving rods in a fluid bed.

Pyrolytic carbon is, by definition, deposited by the pyrolysis of a carbon-containing substance. Accordingly, the core material on which the pyrolytic carbon is deposited will be subject to the fairly high temperature necessary for pyrolysis. Generally, hydrocarbons are employed as the carbon-containing substance to be pyrolyzed, and temperatures of at least about 1000° C are used. Some examples of deposition of pyrolytic carbon are set forth in the aforementioned U.S. Pat. No. 3,298,921. Processes illustrated and described in this patent employ methane as the source or carbon and utilize temperatures generally in the range of about 1200° to 2300° C. Although it is possible to deposit pyrolytic carbon having the desired properties with regard to this invention at somewhat lower temperatures by using other hydrocarbons, for example, propane or butane, it is generally considered that the core material should remain substantially stable at temperatures of at least about 1000° C and preferably at even higher temperatures. Pyrolytic carbons deposited at temperatures below about 1500° C are particularly suited for use in the blood access device 13, because such pyrolytic carbons have exceptional tissue compatibility and mechanical reliability.

Examples of core materials which have the aforementioned stability at high temperatures include artificial graphite, boron carbide, silicon carbide, refractory metals (and alloys), such as tantalum, titanium, molybdenum, tungsten, and various ceramics, such as mullite. A preferred substrate material is polycrystalline graphite. An example of such a graphite is the polycrystalline graphite sold under the trademark POCO.

Vapor-deposited carbon coatings may be applied by the process described in U.S. Pat. No. 3,952,334 "Biocompatible Carbon Prosthetic Devices", issued Apr. 27, 1976. As generally described therein, a substrate is placed in an evaporative coater and a vacuum is established. A crucible within the coater, filled with a commercial grade of artificial graphite, is heated by electron beam bombardment. Coating is carried out until the desired thickness of carbon is deposited and the substrate is then removed. This process results in an exterior carbon layer that is smooth and uniform.

Summarizing, there has been described a device for providing access to the circulatory system of a living body which allows simultaneous withdrawal from and return of blood to the system. The device is biologically compatible with the living tissues in the body and may be implanted in the body and not prevent healing, irritate tissues, or stimulate a strong or prolonged rejection response by the living body. Further, the device is physiologically inert over long periods of time and is mechanically strong and reliable.

While the invention has been described in connection with a preferred embodiment, alternatives, modifications, and variations may be apparent to those skilled in the art in view of the foregoing description. Accordingly, it is intended to embrace all such alternatives, modifications, and variations as fall within the spirit and scope of the appended claims.

What is claimed is:

1. A device to provide access to the circulatory system of a living body for simultaneous withdrawal from and return of blood to the system comprising a pair of parallel tubular conduits of generally circular cross section, either one being insertable in a living blood vessel and the other being connectable to a by-pass graft of that same blood vessel; a generally cylindrical housing having one end closed and extending transversely of and adjoining said conduits near the closed end, the points of adjoining both conduits being spaced apart from each other longitudinally with respect to the axis of the housing and being spaced away from the axis, said housing having fluid communication with each of said conduits through an aperture in the conduit walls at each of said points of adjoining, the perimeter defining each of said apertures being formed of a sharp edge of the conduit wall, said housing having a length sufficient to extend from the blood vessel to a point outside the living body; a valve body in said housing, said valve body having therein a pair of spaced apart ports that are located to be alignable with the apertures at one given rotative position of said valve body, said valve body being adapted to receive a dual-conduit catheter in fluid communication with said ports, one conduit to one port, and said valve body being coaxially rotatable in said housing between positions of alignment and nonalignment of said apertures and said ports to selectively establish fluid communication between the circulatory system and the catheter when inserted in said valve body; at least all blood and skin tissue contacting surfaces of said device being made of a biologically compatible material.

2. A device in accordance with claim 1 further comprising a liner between said valve body and said housing, said liner being affixed to the housing and said valve body rotating therein.

3. A device in accordance with claim 2 wherein the side wall portions of the valve intersect a portion of each of said conduits at each of said aperture locations sufficiently to form a valve seat with each of said conduit walls and a liquid and bacterial seal around said apertures.

4. A device in accordance with claim 3 further comprising a counterbore in the open end of the valve body, a cannula receptacle affixed in said counterbore, and a cap over the open end of said housing, liner, valve body and cannula receptacle, said cannula receptacle having a flange overlying the open ends of the liner and valve body, said cap being of the screw type and having a shoulder for bearing against the flange of the cannula receptacle to provide compression for retaining said valve body in a seated condition in said liner and housing, said cap being provided with a generally circular orifice and a key slot adjacent the circumference of the orifice, and said cap having a circumferential slot in the inner wall thereof adjoining said key slot.

5. A device in accordance with claim 4 further comprising a catheter whose end is inserted through said orifice and into said valve body, said catheter having a lug on its surface extending outwardly at right angles to the axis of the catheter, said key slot serving as a passageway for said lug to enter said circumferential slot, and said lug securing the position of the catheter after rotation of the catheter to engage the lug in said circumferential slot.

6. A device in accordance with claim 5 wherein said catheter includes a pair of flutes in its outer surface and wherein said cannula receptacle includes a pair of longitudinal guides on its inner surface located to engage the flutes of the catheter when the catheter is inserted therethrough, whereby the catheter after being inserted in said valve body may be utilized for rotating said valve body between the positions of alignment and nonalignment of said apertures and said ports.

7. A device in accordance with claim 5 wherein said catheter further includes two parallel isolated conduits, each terminating in fluid communication with one of said ports in said valve body.

8. A device in accordance with claim 7 wherein the two conduits of said catheter are side-by-side.

9. A device in accordance with claim 7 wherein the two conduits of the catheter are concentrically related.

10. A device in accordance with claim 1 further comprising a carbon flange around the perimeter of said housing, said flange having a plurality of holes therethrough, whereby body tissues will grow in and around said holes to stabilize the position of the device implanted in a living body.

11. A device in accordance with claim 10 further including a flexible circumferential flange attached to said carbon flange around its outer diameter, said flexible flange having also a plurality of holes therethrough.

12. A device in accordance with claim 1 wherein the inner portion of said housing tapers to a smaller inner diameter at the closed end and wherein said valve body within said housing tapers to a smaller diameter at its closed end and conforms to the tapered inner portion of said housing in a close-fitting relation.

13. A device in accordance with claim 12 wherein said housing adjoins said conduits at the side of said housing near the closed end of the housing, and wherein the tapered end of the valve body intersects a portion of the wall of each of said conduits at said apertures sufficiently to form a valve seat with said conduit walls and a liquid and bacterial seal around said apertures.

14. A device in accordance with claim 1 wherein said biologically compatible material is carbon.

15. A device in accordance with claim 1 wherein said housing is made of titanium, wherein said liner is pyrolytic carbon, and wherein said valve body is pyrolytic carbon.

16. A device in accordance with claim 2 wherein said cannula receptacle includes a pair of grooves in its outer surface and said valve body includes a pair of grooves on its inner surface located to oppose the pair of grooves in the cannula receptacle and in such opposition forming a cylindrical cavity therebetween, and further including an interlock rod disposed in each cylindrical cavity formed by the opposing grooves.

* * * * *

UNITED STATES PATENT AND TRADEMARK OFFICE
CERTIFICATE OF CORRECTION

PATENT NO. : 4,092,983

DATED : June 6, 1979

INVENTOR(S) : Victor Slivenko

It is certified that error appears in the above-identified patent and that said Letters Patent are hereby corrected as shown below:

Column 1, Line 26, "4" should read --14--.

Column 2, Line 33, "FIGURE 1" should read --FIGURES 1 and 2--.

Column 2, Line 39, "10" should read --19--.

Column 3, Line 48, "cannnula" should read --cannula--.

Column 3, Line 48, "receptable" should read --receptacle--.

Column 4, Line 31, "pasage" should read --passage--.

Column 4, Line 50, "catherter" should read --catheter--.

Column 4, Line 53, "top" should read --tip--.

Column 5, Line 56, "annd" should read --and--.

UNITED STATES PATENT AND TRADEMARK OFFICE
CERTIFICATE OF CORRECTION

PATENT NO. : 4,092,983

DATED : June 6, 1979

INVENTOR(S) : Victor Slivenko

It is certified that error appears in the above–identified patent and that said Letters Patent are hereby corrected as shown below:

Column 5, Line 57, "invention" should read --invasion--.

Column 6, Line 2, after "device 13", "in" should read --is--.

Column 6, Line 43, "servered" should read --severed--.

Column 6, line 66, "possible" should read -- possibly --.

Column 7, line 11, after "has" insert -- as --.

Column 9, Line 21, "or" should read --of--.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks